(12) United States Patent
Biedermann et al.

(10) Patent No.: US 12,042,182 B2
(45) Date of Patent: Jul. 23, 2024

(54) COUPLING DEVICE FOR COUPLING A ROD TO A BONE ANCHORING ELEMENT AND METHOD OF MANUFACTURING THE SAME

(71) Applicant: BIEDERMANN TECHNOLOGIES GMBH & CO. KG, Donaueschingen (DE)

(72) Inventors: Timo Biedermann, Trossingen (DE); Lutz Biedermann, VS-Villingen (DE); Berthold Dannecker, St. Georgen (DE)

(73) Assignee: BIEDERMANN TECHNOLOGIES GMBH & CO. KG, Donaueschingen (DE)

( * ) Notice: Subject to any disclaimer, the term of this patent is extended or adjusted under 35 U.S.C. 154(b) by 0 days.

(21) Appl. No.: 18/298,597

(22) Filed: Apr. 11, 2023

(65) Prior Publication Data
US 2023/0320755 A1    Oct. 12, 2023

Related U.S. Application Data

(60) Provisional application No. 63/329,604, filed on Apr. 11, 2022.

(30) Foreign Application Priority Data

Apr. 11, 2022    (EP) ..................... 22167711

(51) Int. Cl.
*A61B 17/70*    (2006.01)
*A61B 17/68*    (2006.01)
(Continued)

(52) U.S. Cl.
CPC .... *A61B 17/68* (2013.01); *A61B 2017/00526* (2013.01); *A61B 2017/564* (2013.01)

(58) Field of Classification Search
CPC ............ A61B 17/7032; A61B 17/7035; A61B 17/7037
See application file for complete search history.

(56) References Cited

U.S. PATENT DOCUMENTS 9,078,705 B2 * 7/2015 Matthis .............. A61B 17/7002
9,254,150 B2    2/2016 Biedermann et al.
(Continued)

FOREIGN PATENT DOCUMENTS

EP    2 668 919 A1    12/2013
EP    3 158 957 A1    4/2017

OTHER PUBLICATIONS

Extended European Search Report for Application No. 22167711.5, mailed Oct. 6, 2022, 8 pages.
(Continued)

*Primary Examiner* — Eduardo C Robert
*Assistant Examiner* — Michelle C Eckman
(74) *Attorney, Agent, or Firm* — Lewis Roca Rothgerber Christie LLP

(57) ABSTRACT

A coupling device includes a receiving part with an accommodation space for accommodating a head of a bone anchoring element, an opening, and a recess forming two legs for receiving a rod, and a pressure member arranged at least partially in the accommodation space. The pressure member is adjustable from a first configuration where a topmost end of the pressure member is at a first axial position and the head is pivotable in the accommodation space to a second configuration where the topmost end of the pressure member is at a second axial position below the first axial position and the pressure member provisionally lock the heads. At the second configuration, a latching connection is formed to prevent the pressure member from being adjusted back towards the first configuration. The latching connection is
(Continued)

releasable to adjust the pressure member from the second configuration back towards the first configuration.

21 Claims, 11 Drawing Sheets

(51) Int. Cl.
    *A61B 17/00*     (2006.01)
    *A61B 17/56*     (2006.01)

(56) References Cited

U.S. PATENT DOCUMENTS

| | | | |
|---|---|---|---|
| 9,339,302 | B2 | 5/2016 | Biedermann et al. |
| 10,058,367 | B2 | 8/2018 | Biedermann et al. |
| 11,006,981 | B2 | 5/2021 | Melton et al. |
| 2006/0161152 | A1 | 7/2006 | Ensign et al. |
| 2006/0276789 | A1* | 12/2006 | Jackson .................. A61B 17/70 606/301 |
| 2009/0149887 | A1 | 6/2009 | Schlaepfer et al. |
| 2010/0234902 | A1* | 9/2010 | Biedermann ...... A61B 17/7037 606/305 |
| 2011/0152949 | A1* | 6/2011 | Biedermann ...... A61B 17/7037 606/305 |
| 2012/0143266 | A1* | 6/2012 | Jackson ............. A61B 17/7032 606/328 |
| 2014/0142634 | A1* | 5/2014 | Schlaepfer ........... A61B 17/704 29/428 |
| 2016/0331412 | A1* | 11/2016 | Biedermann ...... A61B 17/7037 |
| 2017/0209185 | A1 | 7/2017 | Trautwein et al. |
| 2017/0367843 | A1 | 12/2017 | Eisen et al. |
| 2017/0367845 | A1 | 12/2017 | Eisen et al. |
| 2020/0069337 | A1 | 5/2020 | Jackson et al. |
| 2020/0146724 | A1 | 5/2020 | Italiaie |
| 2020/0155202 | A1* | 5/2020 | Jackson ............. A61B 17/7035 |
| 2021/0114298 | A1 | 4/2021 | Rodriguez Santiago et al. |
| 2021/0169529 | A1 | 6/2021 | Biedermann et al. |
| 2023/0039136 | A1 | 2/2023 | Biedermann et al. |

OTHER PUBLICATIONS

Extended European Search Report for Application No. 21189722.8, mailed Feb. 9, 2022, 9 pages.

* cited by examiner

COUPLING DEVICE FOR COUPLING A ROD TO A BONE ANCHORING ELEMENT AND METHOD OF MANUFACTURING THE SAME

CROSS-REFERENCE TO RELATED APPLICATION(S)

The present application claims priority to and the benefit of U.S. Provisional Patent Application No. 63/329,604, filed Apr. 11, 2022, the contents of which are hereby incorporated by reference in their entirety, and claims priority from European Patent Application EP 22 167 711.5, filed Apr. 11, 2022, the contents of which are hereby incorporated by reference in their entirety.

BACKGROUND

Field

The application relates to a coupling device for coupling a rod to a bone anchoring element, and to a method of manufacturing the same. In particular, the invention relates to a coupling device that forms part of a polyaxial bone anchoring device.

Description of Related Art

Various types of polyaxial bone anchoring devices are known in the art. Usually, a polyaxial bone anchoring device includes a coupling device and a bone anchoring element with a head that is pivotably received in the coupling device and can be locked at a desired angle of the bone anchoring element relative to the coupling device. The coupling device also receives a rod that is configured to connect the polyaxial bone anchoring device to a further bone anchor. U.S. Pat. No. 9,339,302 B2, for example, describes such a polyaxial bone anchoring device. The document also describes a two-part locking member for a polyaxial bone anchoring device that is manufactured using an additive manufacturing method.

In U.S. Pat. No. 9,254,150 B2, another polyaxial bone anchoring device is described that includes a receiving part with a seat for receiving a head of a bone anchoring element and a channel for receiving a rod to be connected to the bone anchoring element. The bone anchoring element is pivotable with respect to the receiving part and can be fixed at an angle by exerting pressure via a pressure element onto the head. The pressure element includes a spring element that engages a portion of the receiving part via a detent connection, so that the pressure element can be held in a position that allows pivoting of the anchoring element.

SUMMARY

It is an object of the invention to provide a coupling device for coupling a bone anchoring element to a rod, in particular in a polyaxial manner, where the coupling device is improved and/or is otherwise an alternative compared to conventional coupling devices, and a method of manufacturing such a coupling device.

According to an aspect of the invention, a coupling device for coupling a rod to a bone anchoring element includes a receiving part having a first end and a second end, a central longitudinal axis extending through the first end and the second end, an accommodation space for accommodating a head of the bone anchoring element with an opening at the second end, and a recess for receiving the rod, the recess defining two free legs, and a pressure member arranged at least partially in the accommodation space. The pressure member is movable from at least a first position where an inserted head is pivotable in the accommodation space and a second position where the pressure member exerts pressure onto the inserted head such that the head is provisionally locked. In the second position, the pressure member is configured to engage the receiving part by a latching connection such that the pressure member is at least temporarily prevented from moving to the first position.

When the pressure member is in the second position, the head can be provisionally locked without interaction between a rod and/or a fixation member with the receiving part or the pressure member. Moreover, the head can remain in the provisionally locked configuration without use of an instrument. This allows a practitioner to carry out adjustment steps in a convenient and time saving manner.

According to an aspect of the invention, the pressure member can be moved into the second position by engaging an actuating portion of the pressure member that protrudes above the first end of the receiving part. This may reduce the required lateral space for an instrument to engage the pressure member.

According to a further aspect of the invention, in the provisional locking position of the pressure member, the head may be prevented from pivoting by a first clamping force. In a final locking position of the pressure member, the head may be prevented from pivoting by a second clamping force greater than or equal to the first clamping force. The second clamping force can be achieved by using a tool or a locking member, for example a locking screw, that acts onto the pressure member, for example via an inserted rod.

According to a further aspect of the invention, the latching connection between the pressure member and the receiving part can be released. Thereby, the pressure member can be moved out of the second position to release the provisional locking of the head. The actuating portion, preferably the arms of the pressure member, may be flexible, in particular resilient. Preferably, the actuating portion may be axially flexible. Further preferably, the actuating portion may be flexible in a direction transverse to the central axis. By exerting a force onto the actuating portion, preferably transverse to the axial direction, the actuating portion is bent and the pressure member can be moved out of the second position. Thus, the step of provisionally locking and releasing the head can be carried out several times. Due to the flexibility of the arms of the pressure member, tolerances in the dimensions of the parts may be balanced.

According to a still further aspect of the invention, the engagement of the pressure member with the receiving part in the second position produces a tactile feedback for the user. Thereby the realization of the second position can be safely determined.

According to a still further aspect of the invention, the receiving part and the pressure member are interconnected parts which are movable relative to each other but are inseparable prior to using the coupling device and/or during use. In other words, under conditions of use prior or during surgery and in the implanted state, the receiving part and the pressure member cannot be separated from each other without damaging or destroying (i.e., permanently deforming) the coupling device. Hence, the coupling device is free from separate fixation members that keep the receiving part and the pressure member together. The coupling device may therefore include less parts. In addition, the parts are safely secured together.

In a particular embodiment of the invention, the coupling device is configured to provide a bottom-loading polyaxial bone anchoring device, which allows a practitioner to insert the head of the bone anchoring element from the bottom end of the coupling device. Alternatively, the coupling device may be designed for a top-loading polyaxial bone anchoring device, where the bone anchoring element is inserted from the top end of the receiving part into the coupling device.

A polyaxial bone anchoring device according to embodiments of the invention includes, in addition to the coupling device, a bone anchoring element having a head and a shank, preferably where the head has a spherically-shaped outer surface portion.

The coupling device may be made using an additive manufacturing method, more specifically, an additive layer manufacturing method. In such a method, the coupling device is built up by layer-wise deposition of a building material and solidifying or melting the material in each layer based on the cross-section of the coupling device in the respective layer. A suitable method is, for example, selective laser sintering (SLS) or selective laser melting (SLM), in which the building material is a powder, such as a metal powder or a plastic powder, and a laser is used to melt the powder. Alternatively, an electron beam may be used. Also, other known methods of powder based three-dimensional printing in which layers of a powder material are deposited and solidified by applying a binder material at positions corresponding to the coupling device may be used. Still further additive manufacturing methods, for example, fused deposition modeling (FDM), may also be applied.

Hence, the receiving part and the pressure member may have complex shapes and/or may be interconnected in a manner that may be difficult or impossible to manufacture conventionally. Thereby, an improvement with regard to the strength of the parts and an improved transfer of forces may be achieved. Moreover, using an additive manufacturing method for manufacturing the coupling device may be more cost efficient than using a conventional manufacturing method.

In a particular embodiment of the invention, the receiving part and the pressure member can be built up as a monolithic unit. The receiving part and the pressure member may be separated after they have been manufactured with the additive manufacturing method. More specifically, the monolithic unit may include a holding portion that is configured to hold the monolithic unit with a tool to allow separation of the receiving part and the pressure member from the holding portion by cutting. This allows a practitioner to precisely separate the receiving part and the pressure member at a specific or desired position. As a result of the separation, the receiving part and the pressure member form an integrated unit.

It shall be noted that the additive manufacturing method, in particular, an additive layer manufacturing method, may influence the appearance of the coupling device. For example, the layers may be visible on the surface of the finished object, even if the integrated unit including the receiving part and the pressure member is post-treated, such as polished, etched, coated or otherwise treated. It may also be possible to identify traces of the laser or electron beam when inspecting the fabricated object. Hence, the additive manufacturing method, in particular the additive layer manufacturing method, can be distinguished on the basis of the finished object or product compared to a conventional subtractive manufacturing method. Alternatively or in addition, the use of an additive manufacturing method may be identified on the basis of the geometry of the manufactured coupling device, for example, if such a geometry is not suitable for conventional manufacturing.

BRIEF DESCRIPTION OF THE DRAWINGS

Further features and advantages of the invention will become apparent from the description of embodiments by means of the accompanying drawings. In the drawings.

DETAILED DESCRIPTION

Figure 1:
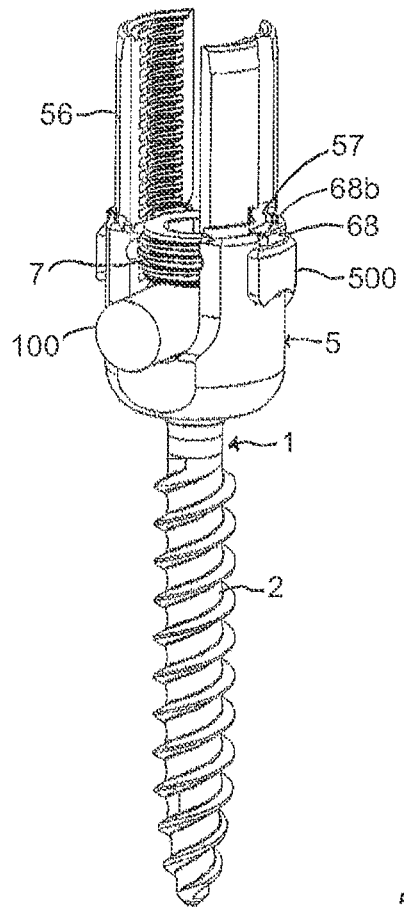
FIG. 1 shows a perspective view of a polyaxial bone anchoring device with a coupling device according to a first embodiment.
Figure 2:
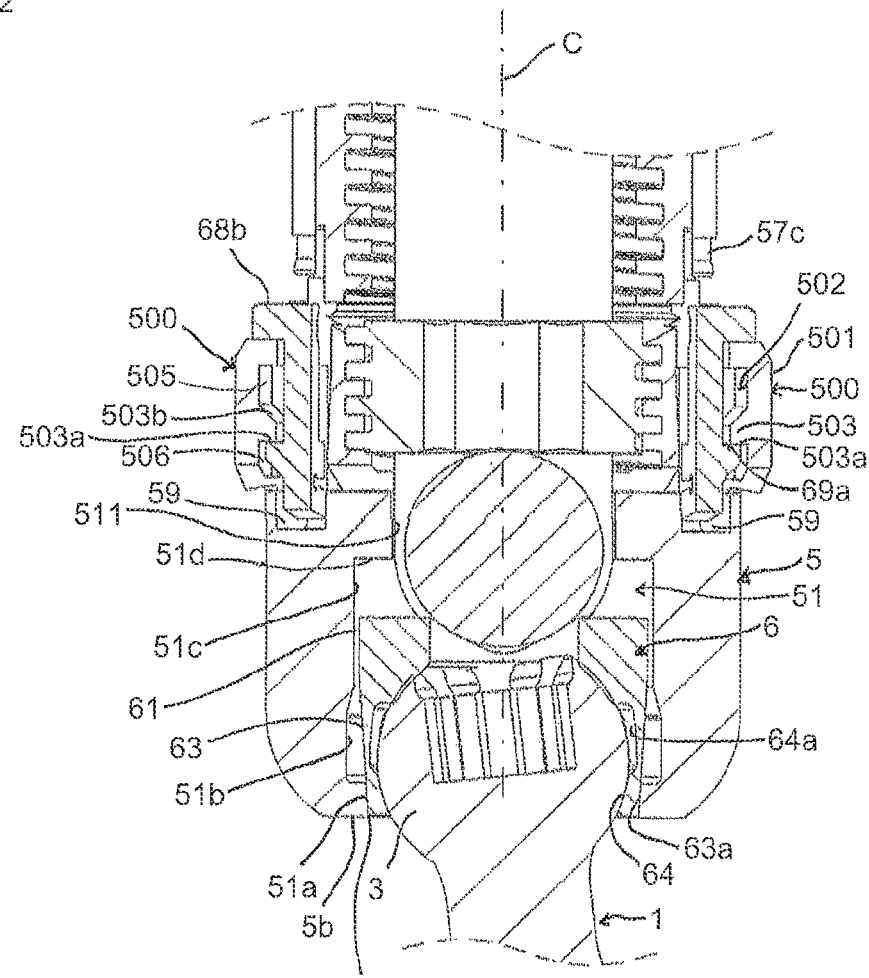
FIG. 2 shows an enlarged cross-sectional view of a portion of the polyaxial bone anchoring device of FIG. 1, the cross-section taken in a plane perpendicular to a rod axis of an inserted rod.
Figure 3:
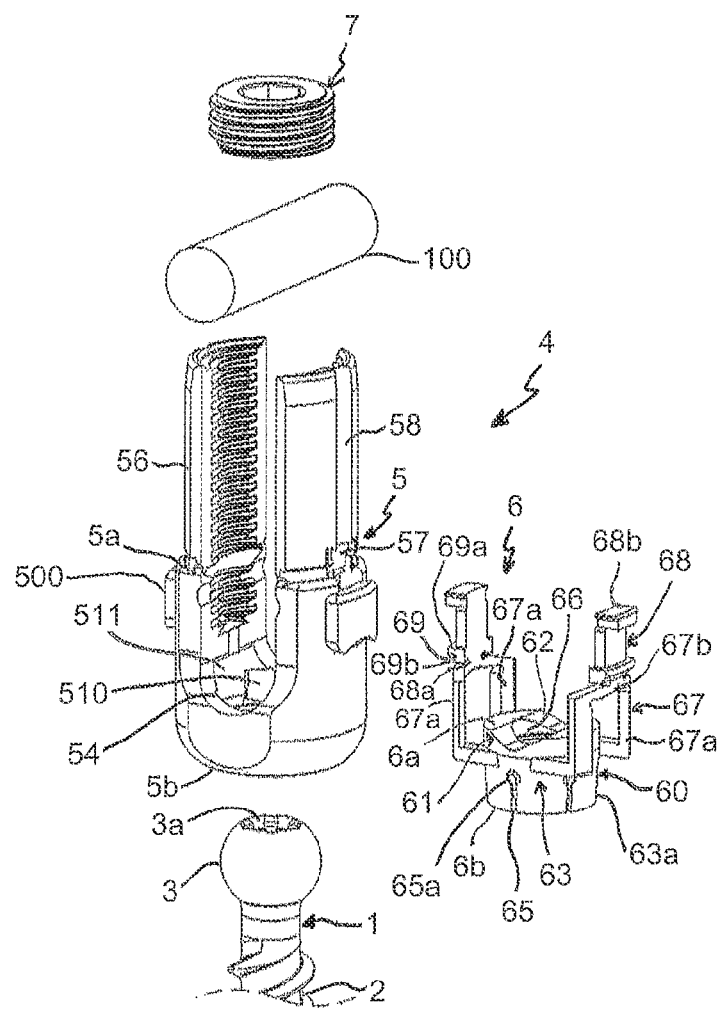
FIG. 3 shows an exploded view of the polyaxial bone anchoring device of FIGS. 1 and 2, where a pressure member of the bone anchoring device is shown separated from a receiving part of the bone anchoring device for illustration purposes only.
Figure 4:
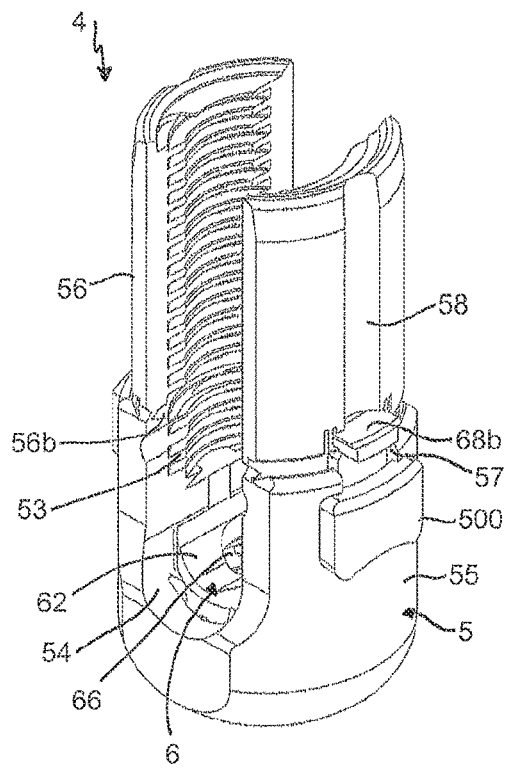
FIG. 4 shows a perspective view from a top of a coupling device of the bone anchoring device of FIGS. 1 to 3, where the coupling device includes the receiving part and the pressure member.
Figure 5:
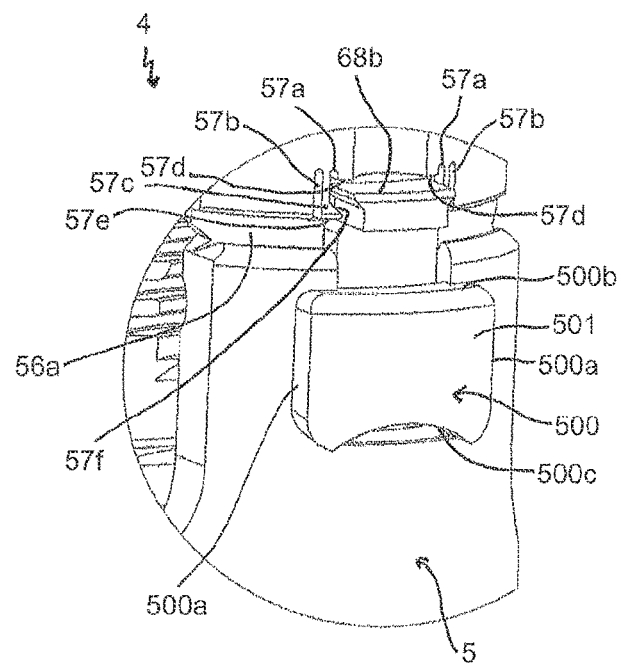
FIG. 5 shows an enlarged view of a detail of FIG. 4.
Figure 6:
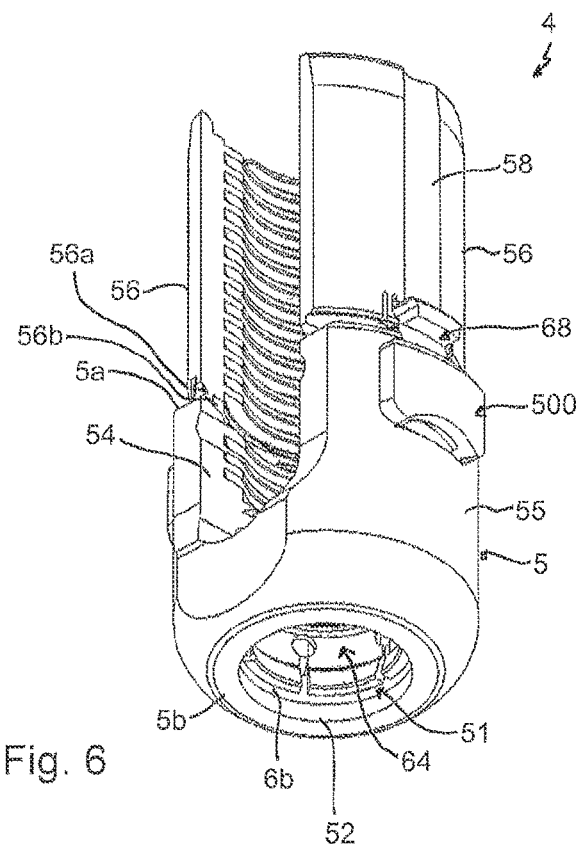
FIG. 6 shows a perspective view from a bottom of the coupling device of FIGS. 4 and 5.
Figure 7:
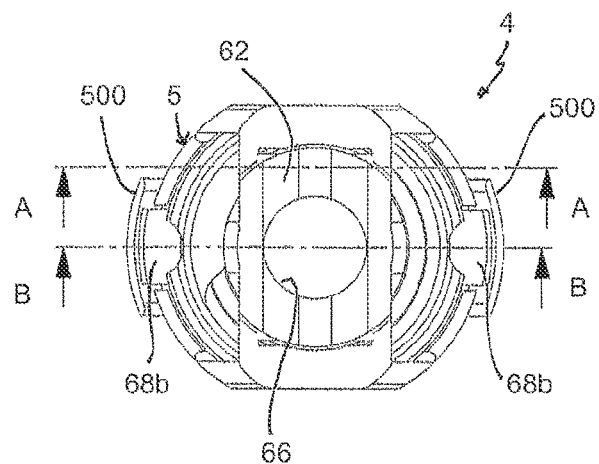
FIG. 7 shows a top view of the coupling device of FIGS. 4 to 6.
Figures 8, 9:
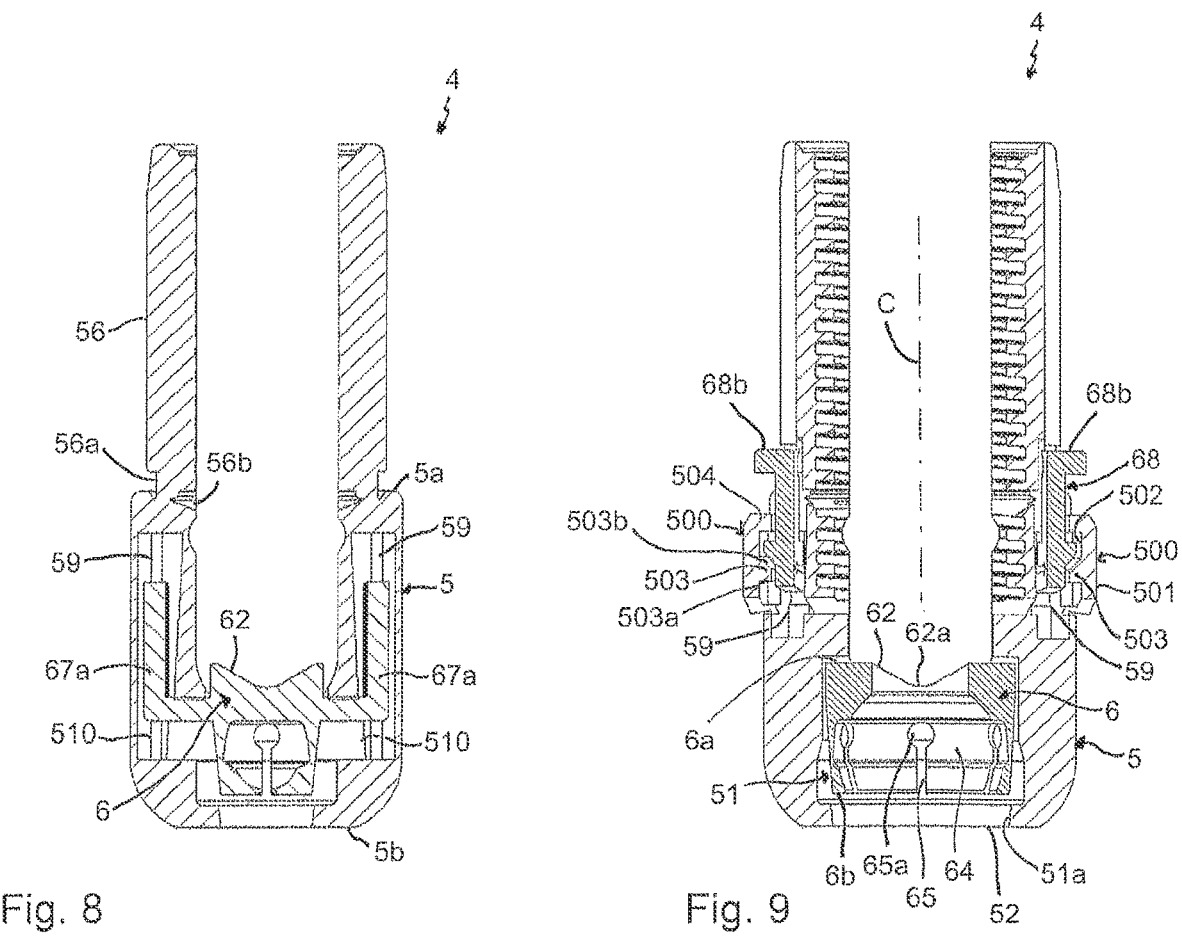
FIG. 8 shows a cross-sectional view of the coupling device of FIGS. 4 to 7, the cross-section taken in a plane along line A-A in FIG. 7.
FIG. 9 shows a cross-sectional view of the coupling device of FIGS. 4 to 7, the cross-section taken in a plane along line B-B in FIG. 7.

A polyaxial bone anchoring device according to a first embodiment, which is generally shown in FIGS. 1 to 3, includes a bone anchoring element 1 in the form of a screw member having a threaded shank 2 and a head 3. On its free end, the head 3 may have a recess 3a for engagement with a tool. The bone anchoring device further includes a coupling device 4 for connecting the bone anchoring element 1 to an elongate stabilization member, such as a rod 100. The coupling device 4 has an integrated unit including a receiving part 5 and a pressure member 6 that are inseparably interconnected with each other. In FIG. 3, the receiving part 5 and the pressure member 6 are shown as separate parts for illustration purposes only. For securing the rod 100 in the receiving part 5 and to exert pressure onto the pressure member 6, a locking element 7 in the form of, for example, a set screw which cooperates with the receiving part 5 may further be provided.

Referring further to FIGS. 4 to 9, the receiving part 5 is a substantially cylindrical part, preferably a monolithic part, and has a first or top end 5a, a second or bottom end 5b, and a passage 51 extending from the top end 5a towards the bottom end 5b, the passage 51 defining a longitudinal central axis C. The top end 5a forms the uppermost end of the receiving part in the final state when extensions have been removed, as explained below. By the passage 51, an opening 52 at the bottom end 5b is defined, which has a width that is greater than a greatest width of the head 3, so that the head 3 of the bone anchoring element 1 is insertable through the opening 52. The passage 51 may have several sections with different widths and/or shapes, and is not limited to the exact shape shown in the figures. Adjacent to the opening 52, a narrowing section 51a is provided which narrows, for example conically, towards the bottom end 5b. The narrowing section 51a cooperates with a portion of the pressure member 6, such that a compressive force is exerted via the pressure member 6 onto an inserted head 3. A widened section 51b follows the narrowing section 51a in a direction towards the top end 5a. The widened section 51b forms part of an accommodation space configured to accommodate a portion of the pressure member 6 and the head 3. A portion of the pressure member 6 is configured to expand in the accommodation space to permit the head 3 to enter and to be inserted into the pressure member 6. Further, the passage 51 may have an intermediate section 51c that has a smaller width than the widened section 51b, and permits a portion of the pressure member 6 to slide therein in an axial direction. A threaded bore 53 with an internal thread configured to cooperate with the locking member 7 extends from the top end 5a in the direction of the bottom end 5b. Moreover, a substantially U-shaped recess 54 that starts from the top end 5a defines two free legs 55 that form a channel for receiving the rod 100. A longitudinal axis of the substantially U-shaped recess 54 is coaxial with or parallel to a longitudinal axis of the rod 100 when the rod is inserted. As can be seen in particular in FIG. 2, a shoulder 51d limits the accommodation space towards the top end 5a by forming an abutment.

Two extensions 56 project from the legs 55 above the top end 5a, respectively. The extensions 56 may serve during surgery for guiding the rod and the fixation member to the coupling device. This may be particularly useful in minimally invasive surgery (MIS). In greater detail, the extensions 56 form extended portions of the legs 55 and may be monolithically formed with the legs 55, respectively, via weakened sections 56a that have a reduced radial thickness. An internal groove 56b provided at the axial position of the weakened section 56a may further facilitate breaking off of the extensions 56 from the legs 55. Breaking off of the legs may be accomplished, for example, after the locking member 7 has been inserted and the polyaxial bone anchoring device has been finally locked with the rod 100. The extensions 56 have an inner diameter that matches the inner diameter of the coaxial bore of the receiving part 5, and the internal thread 53 continues from the legs 55 into the extensions 56. An outer diameter of the extensions 56 may be reduced compared to the outer diameter of the legs 55.

In a circumferential direction at the center of each of the legs 55 and the corresponding extensions 56, a recess 57 is formed that defines an opening through which a portion of the pressure member 6 can extend. As can be seen in particular in FIGS. 3 to 6, on the left side and the right side of each recess 57, first axial slits 57a extend into the extensions 56. To the left of a left one of the first axial slits 57a and to the right of a right one of the first axial slits 57a, second axial slits 57b extend into the extensions 56 that are somewhat longer than the first axial slits 57a such that flexible tongs 57c between the axial slits 57a, 57b are formed. A lower edge of the extensions 56 that lies between the first axial slits 57a forms a first abutment 57d for a portion of the pressure member 6. The first abutment 57d limits upper movement of the pressure member 6 and define an insertion position of the pressure member 6. A lower edge of the flexible tongs 57c forms a second abutment 57e for the pressure member 6. The tongues 57c may have an inclined surface 57f along which a portion of the pressure member 6 can slide when the pressure member 6 is moved downwards to spread apart the tongues 57c. The second abutment 57e defines a pre-locking position of the pressure member 6. In addition, an axially extending groove 58 may be formed that extends from a free end of the extensions 56 up to the recess 57 and that may provide guidance for an instrument that is configured to actuate the pressure member 6.

Next, the receiving part 5 has inside each of the legs 55, substantially at the center thereof in a circumferential direction, a slot 59 that is shaped such that a portion of the pressure member can extend therethrough. The slot 59 may have a depth or axial extension that corresponds to an axial position below the internal thread of the bore 53, and a width in a circumferential direction that is greater than a width of the recess 57. In greater detail, the width of the slot 59 in the circumferential direction allows arms of the pressure member 6 to extend therein. On the other hand, the slot 59 is in communication with the accommodation space 51*b*, 51*c* of the receiving part 5 via four openings 510 through which a portion of the pressure member can extend into the slot 59, as can be seen, for example, in FIGS. 3 and 7 to 9. Moreover, in the middle of each of the legs 55 in the circumferential direction, a protrusion 500 is formed at the outer surface of the receiving part 5 that defines an outer wall portion limiting the slot 59. The protrusion 500 includes an outer surface 501 and an inner surface 502 that may both be substantially cylindrical. The inner surface 502 includes an engagement portion in the form of a rib-like inner protrusion 503 located axially approximately in the middle of the protrusion 500. The rib-like inner protrusion 503 has a lower side 503*a* that may be substantially perpendicular to the central axis C and an inclined upper side 503*b*, the inclination of which is such that a portion of the pressure member can slide thereon when the pressure member is moved downward. By the inner protrusion 503, a latching portion is formed that allows the pressure member 6 to snap thereunder. As can be seen in particular in FIG. 2 and FIG. 9, the inner wall 502 of the protrusion 500 is divided by the rib-like inner protrusion 503 into an upper space 505 and a lower space 506. The upper space 505 serves for accommodating an engagement portion of the pressure member when the pressure member is in an insertion position. The lower space 506 serves for accommodating the engagement portion of the pressure member 6 when the pressure member 6 is in the provisional locking position and/or in the final locking position. An outer contour of the protrusion 500 may be substantially rectangular when seen in a side view, for example, in FIG. 13, with two vertically extending short sides 500*a*, an upper circumferentially extending long side 500*b* that connects the short sides 500*a*, and a lower long side 500*c* that may be concavely shaped. By means of the concavely-shaped lower long side 500*c* of the protrusion 500, a portion of the slot 59 may be exposed to the outside.

Lastly, in the section 51*c* of the receiving part 5, a shallow cylindrical recess 511, as particularly visible in FIG. 3, is formed to receive a portion of the pressure member 6 that supports the rod. The transverse holes 510 that are arranged between the accommodation space 51*b*, 51*c* and the slot 59 are arranged at each side of this recess 511.

The pressure member 6, preferably a monolithic piece, is formed with the receiving part as an integrated unit, or in other words, the pressure member is assembled to the receiving part in a manner in which the pressure member cannot be fully separated from the receiving part. FIG. 3 shows the pressure member as a separate part for explanation of its features only. The pressure member 6 includes a main body 60 having a first end or top end 6*a* and a second end or bottom end 6*b*. Adjacent to the top end 6*a*, there is a substantially cylindrical upper portion 61 with an outer diameter that permits the main body 60 to move in the axial direction in the section 51*c* of the accommodation space. At the top end 6*a*, a rod receiving recess 62 is formed that provides a rod support surface. The rod support surface may have a substantially V-shaped cross-section with a longitudinal axis extending substantially perpendicular to a cylinder axis of the upper portion 61. Such a cross-section of the rod support surface allows rods of different diameters to be similarly received by the rod support surface. A depth of the rod receiving recess 62 may be smaller than a diameter of the rod 100, such that when the rod 100 rests on the rod support surface, the rod projects over the top end 6*a* of the main body 60, as shown, for example, in FIG. 2. A lower portion 63 of the pressure member 6 adjacent to the cylindrical portion 61 has a tapered, preferably conical, outer surface. A lowermost region 63*a* of the lower portion 63 adjacent to the bottom end 6*b* is configured to cooperate with the narrowing section 51*a* of the receiving part 5. In the lower portion 63, a head receiving recess 64 is formed that extends from the bottom end 6*b* to a distance from a bottom 62*a* of the rod receiving recess 62. The head receiving recess 64 has a substantially hollow spherical shape, with a radius of the sphere substantially matching that of the head 3, and thus forms a seat for the head 3 to pivot. At around a region of the head receiving recess with the largest diameter, a circumferential cut-out 64*a* may be provided that enlarges the head receiving recess 64. This may facilitate spreading of the head receiving recess 64 for inserting the head 3. In addition, in the lower portion 63 of the main body 60 of the pressure member 6, a plurality of axial slits 65 that are open towards the bottom end 6*b* are provided which render the lower portion 63 flexible. To obtain a certain degree of flexibility, the slits 65 may widen towards their closed end 65*a*. The axial extension of the slits 65 may reach up to the upper region of the cut-out 64*a* in some embodiments.

Furthermore, the main portion 60 of the pressure member 6 has a coaxial bore 66 for allowing access to the head 3, more particularly to the recess 3*a* of the head 3, with a tool.

On the left and on the right side of the rod receiving recess 62 of the main body 60, upstanding arms 67 are formed that project to the side and upwards from the main portion 60. The arms 67 are mirror-symmetrical to a plane extending through the central longitudinal axis C and the longitudinal axis of the rod receiving recess 62. In the following, one of the arms 67 will be described in greater detail. Each arm 67 has two substantially L-shaped base portions 67*a* that are connected, preferably monolithically, via their short sides to the conical section 63 of the main portion 60. On their long sides, the base portions are connected by a yoke portion 67*b*. An outer and an inner surface of the base portion 67*a* and the yoke portion 67*b* may be cylindrical, and the long sides may be formed as thin strips that extend in an axial direction. The size of the base portions 67*a* is such that the base portions 67*a* are configured to extend through the openings 510 of the receiving part 5 into the slot 59. In other words, the yoke portion 67*b* is fully arranged in the slot 59, and the base portions 67*a* are configured to move axially in the openings 510, respectively. In the middle of the yoke portion 67*b* in the circumferential direction, an actuating portion 68 extends upwards. The actuating portion 68 has a circumferential width smaller than that of the yoke portion 67*b*, such that the actuating portion fits into the slot 59 and also can project out of the slot 59 into the recess 57. A connection section between the actuating portion 68 and the yoke portion 67*b* is narrowed by two lateral slits 68*a*. Generally, the arms 67, and more specifically the actuating portion 68, is flexible to some extent in the axial direction and in a direction transverse to the axial direction. As a result thereof, the actuating portion 68 can be slightly compressed towards the main portion 60 in the axial direction. In addition, the actuating portion 68 can be bent inwards in the radial direction. Preferably, the actuating portion 68 is resiliently compressible in the axial and/or radial direction and resumes its original position once a pressure acting thereupon is relieved.

An upper side 68b of the actuating portion, which is provided on an outwardly extending rim, is configured to abut against the first abutment 57d on the extensions 56 when the pressure member 6 is in the insertion position, or against the second abutment 57e when the pressure member 6 is in the pre-locking position. Adjacent to the yoke 67b, the actuating portion 68 includes an outwardly protruding rib-like engagement portion 69. The engagement portion 69 has a flat upper surface 69a and an inclined lower surface 69b, the inclination of which may correspond to that of the inclined portion 503b of the inner protrusion 503 of the protrusion 500. The upper side 69a of the engagement portion 69 is configured to snap under the protrusion 503 of the receiving part 5. Moreover, after snapping under the protrusion 503, the upper side 69a of the engagement portion 69 is configured to abut against the lower side 503a of the projection 503 to provide a latching connection.

The pressure member 6 is arranged in the receiving part 5 such that the main portion 60 is located in the accommodation space, at least in the section 51c, and the arms 67 extend into and inside the legs 55 of the receiving part. The upper rim of the actuating portion 68 with the end surface 68b extends out of the legs 55 into the recess 57 provided at the extensions 56. Specifically, the receiving part 5 and the pressure member 6 are interconnected parts which are movable relative to each other but are inseparable prior to using the coupling device and/or during use. In other words, under conditions of use prior or during surgery and in the implanted state, the receiving part 5 and the pressure member 6 cannot be separated from each other without damaging or destroying the coupling device.

The pressure member 6 is movable in the receiving part 5 in a manner such that it can assume several positions. An insertion position of the pressure member 6, in which the head 3 can be inserted, is defined in that the pressure member 6 abuts with the upper surface 68b of the actuating portion 68 against the first abutment 57d in the extension 56. Simultaneously, the main body 60 of the pressure member 6 is in an upper portion of the section 51c of the passage 51 and the engagement portion 69 is located in the upper space 505 of the inner wall 502 of the protrusion 500. A pre-locking position is defined in that the pressure member 6 abuts with the upper surface 68a against the second abutment 57e in the extension 56. An inserted head is still pivotable but cannot be removed through the lower opening 52. It should be mentioned that in the pre-locking position the head may be held in the pressure member 6 by friction, so that the head can be pivoted only if a force is applied that overcomes the friction force. In a provisional locking position of the pressure member 6 relative to the receiving part 5, the engagement portion 69 is in the lower groove 506 and the upper surface 69a of the engagement portion 69 abuts against the lower surface 503a of the projection 503 of the receiving part 5. In this provisional locking position, the lower section 63a of the conical outer surface 63 of the pressure member 6 engages the conical inner surface portion 51a adjacent to the lower opening 52 of the receiving part 5 to an extent such that the head receiving recess 64 of the pressure member 6 is compressed and the head 3 cannot pivot, i.e., is locked or clamped with a first force. A final locking position is defined where the pressure member 6 has engaged the narrowing portion 51a of the receiving part to an extent such that the head is locked with a second force greater than the first force. This can be achieved by tightening the locking member 7.

The coupling device and parts thereof, as well as the bone anchoring element and the locking element and the rod, may be made of any bio-compatible material, preferably, however, of titanium or stainless steel or of any other bio-compatible metal or metal alloy or plastic material. For bio-compatible alloys, a NiTi alloy, for example Nitinol, may be used. Other materials that can also be used include magnesium or magnesium alloys. Bio-compatible plastic materials that can be used may be, for example, polyether ether ketone (PEEK) or poly-L-lactide acid (PLLA). The coupling device and other parts of the polyaxial bone anchoring device may be made of the same or of different material or materials.

Preferably, the coupling device is manufactured using an additive manufacturing method. In an additive manufacturing method, the coupling device is built up layer-by-layer based on three-dimensional data that characterize the shape and the size of the coupling device. As an example, a powder based layer manufacturing technique, such as selective laser-melting (SLM), includes the steps of applying a layer of building material, such as a powder, in particular a metal powder or a plastic powder, onto a support surface, and selectively solidifying or melding the powder at positions corresponding to the cross-section of the coupling device in the respective layer. Subsequently, the steps of applying and melting further layers of the coupling device are repeated until a coupling device is finished. The data of the cross-section of the coupling device for each respective layer and the data for controlling the layer manufacturing apparatus result from CAD or CAM data of the coupling device and corresponding slice data. In particular undercuts and complex shapes can be built-up. In the present embodiment, for example, the extension of the arms of the pressure member through the legs of the receiving part would almost be impossible to manufacture in a conventional subtractive manufacturing method, which would require manufacturing of the parts in several sub-parts to realize the complex shape.

Figure 10:
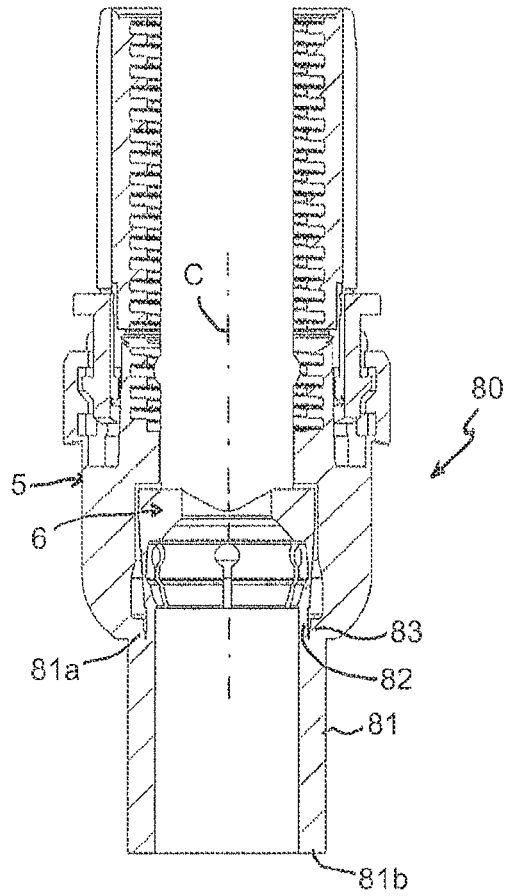
FIG. 10 shows a cross-sectional view of a step of manufacturing the coupling device according to FIGS. 4 to 9, the cross-section taken in a plane extending through centers of legs of the receiving part and including a central axis of the receiving part.
Figure 11:
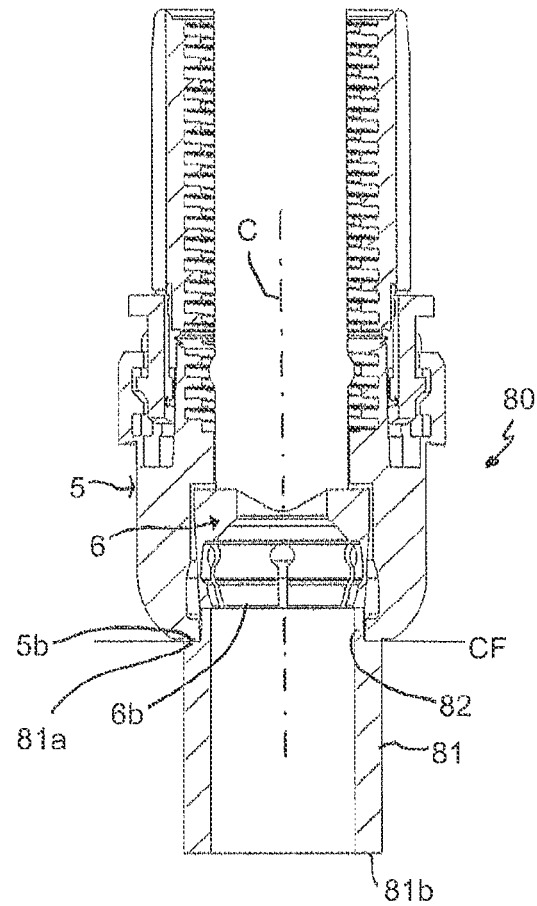
FIG. 11 shows a cross-sectional view of the step of manufacturing shown in FIG. 10, with a cutting line indicating a step of cutting away a holding portion of the coupling device.

An embodiment of a method of manufacturing the coupling device will be described, referring to FIGS. 10 and 11. The receiving part 5 and the pressure member 6 are manufactured using an additive layer manufacturing technique as a monolithic unit 80. The monolithic unit 80 includes a holding portion 81 that is monolithically connected to the receiving part 5 and also to the pressure member 6. In the example shown, the holding portion 81 is a tube-shaped portion with an upper end 81a and a lower end 81b. The upper end 81a includes an inner tube portion 82 that is monolithically connected to the second end 6b of the main portion 60 of the pressure member 6. At a small distance therefrom in the radial direction, an outer tube portion 83 is monolithically connected to the second end 5b of the receiving part 5. The contour of the narrowing portion 51a may be separated or spaced apart from the inner tube portion 82, for example, in the radial direction.

A predetermined cutting face CF is defined at the second end 5b of the receiving part 5 and extends inside the receiving part up to and along the second end 6b of the pressure member. The predetermined cutting face CF may be marked, for example through externally visible markings that are generated during the layer-wise build-up and/or internal structures that facilitate the cutting, for example a weakened area. When the monolithic unit 80 has been built-up, unmelted or unsolidified building material can be removed through the tube of the holding portion 81, or for example, through the openings which connect the slot 59 with the inside of the receiving part or with the outside.

Once separated, the integrated unit including the receiving part 5 and the pressure member 6, may be further treated, for example polished, sandblasted, etched, or coated. However, in some applications no post-treatment is carried out, since a rough surface that may result from the building process may be desirable.

Figure 12:
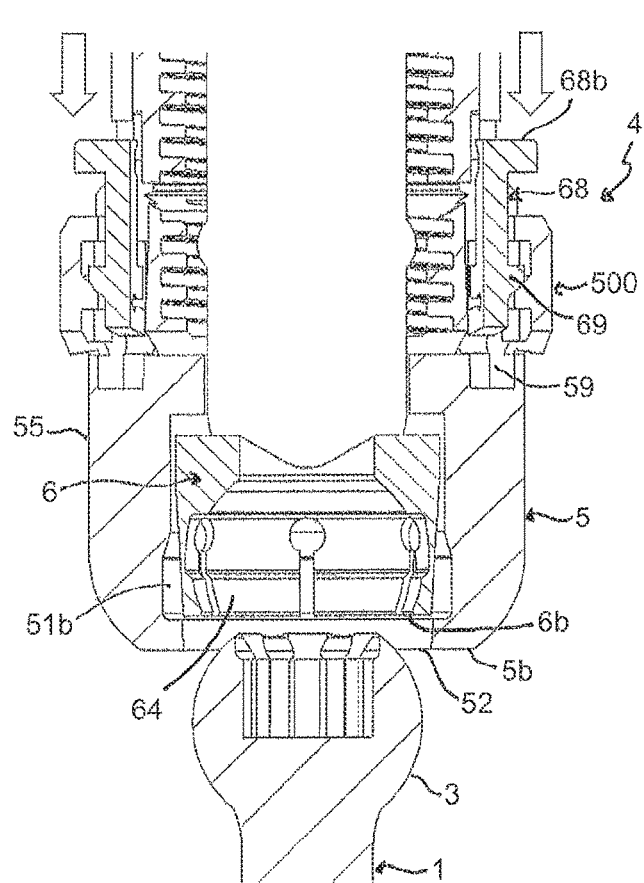
FIG. 12 shows a cross-sectional view of a step of assembling the polyaxial bone anchoring device of FIGS. 1 to 9, in which a head of a bone anchoring element is inserted through a lower opening of the receiving part.
Figure 13:
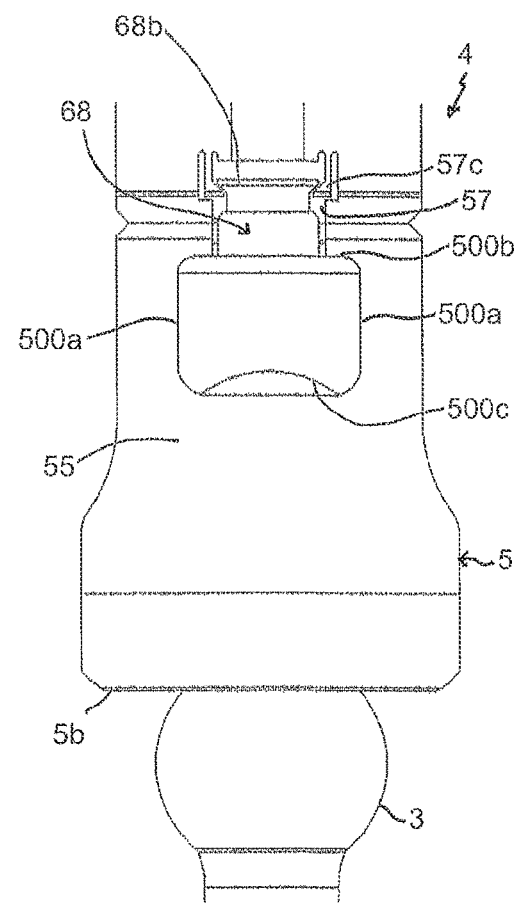
FIG. 13 is a side-view of the step of assembling the polyaxial bone anchoring device corresponding to FIG. 12.

Steps for assembling the polyaxial bone anchoring device of FIGS. 1 to 3 will be described, referring to FIGS. 12 to 19. In a first step, as shown in FIGS. 12 and 13, the pressure member is in a position in which the main portion 60 of the pressure member 6 is in an upper region of the section 51b, 51c of the passage 51. In particular, the lower end 6b is within the accommodation space 51b so that the lower end 6b can expand when the head 3 is inserted. The actuating portion 68 protrudes out of the recess 57 of the extension member 56, but does not yet abut against the abutment 57d of the extension member 56. When the bone anchoring element 1 is already inserted into bone, the receiving part 5 with pressure member 6 is placed onto the head 3, and the head 3 is introduced through the lower opening 52.

Figure 14:
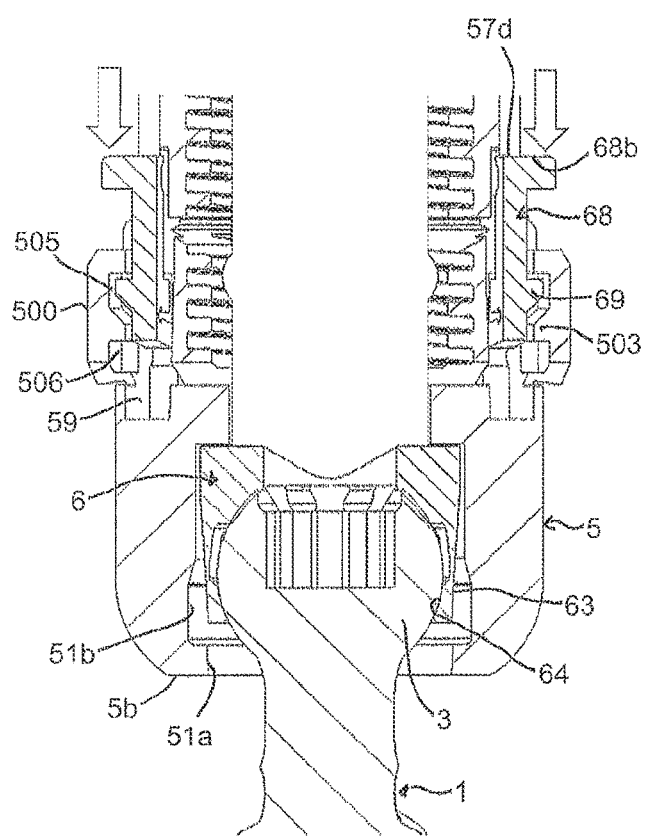
FIG. 14 is a cross-sectional view of a further step of assembling the polyaxial bone anchoring device of FIGS. 1 to 9, in which the pressure member is in an insertion position and the head of the bone anchoring element is fully inserted into the pressure member.
Figure 15:
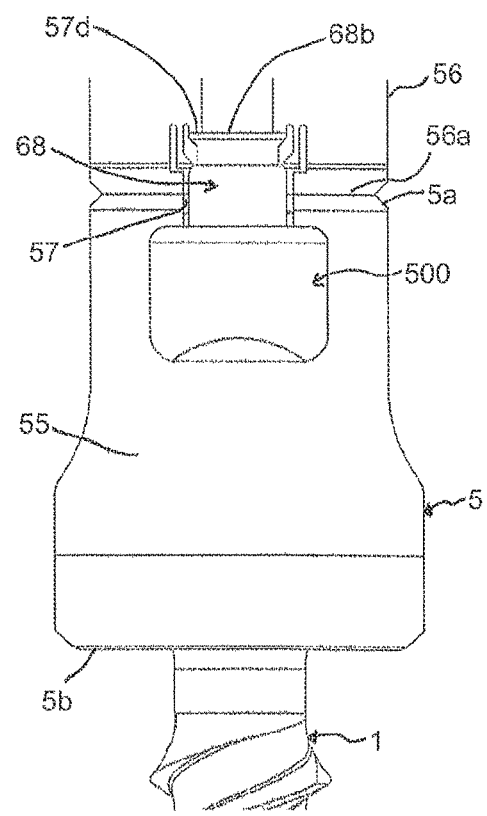
FIG. 15 is a side-view of the step corresponding to FIG. 14.

Next, as shown in FIGS. 14 and 15, the head is inserted into the head receiving recess 64 of the pressure member 6. This is possible, since the head 3 widens the head receiving recess 64 while entering and being inserted into the pressure member due to the flexibility of the conical portion 63. Thereby, the head 3 moves the pressure member 6 upwards until the end surface 68b of the actuating portion 68 abuts against the abutment 57d at the extension 56. This is the insertion position, in which the head 3 is or can be fully inserted.

Figure 16:
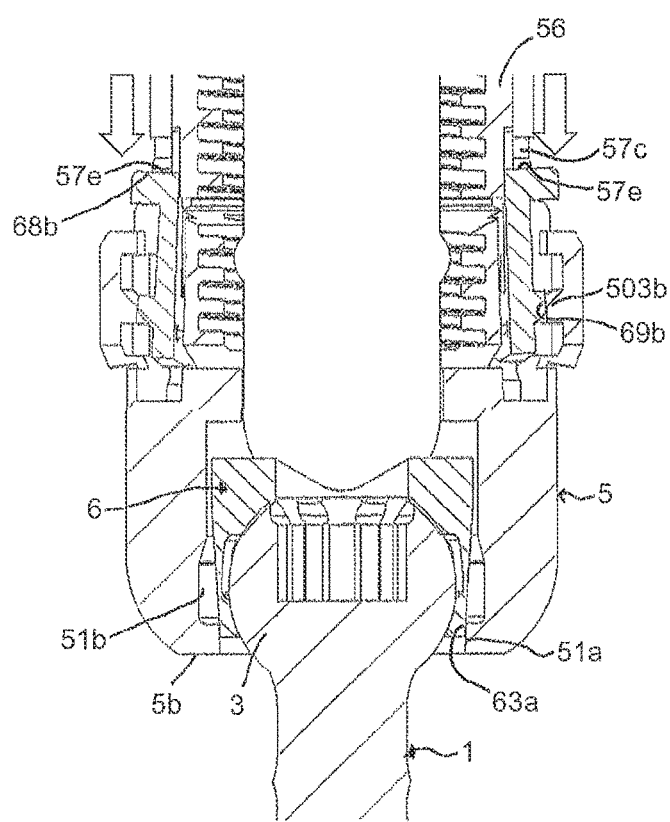
FIG. 16 shows a cross-sectional view of the polyaxial bone anchoring device of FIGS. 1 to 9, where the pressure member is in a pre-locking position in which the head of the bone anchoring element is prevented from removal through the lower opening but is still pivotable in the receiving part.
Figure 17:
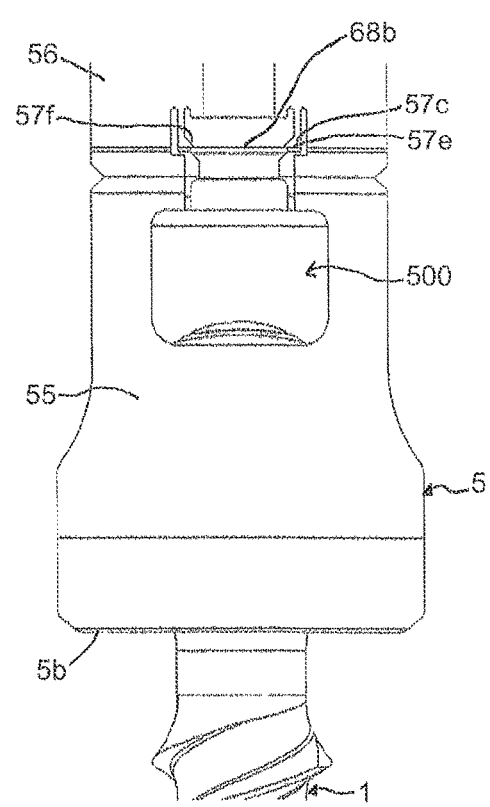
FIG. 17 is a side-view of the polyaxial bone anchoring device corresponding to FIG. 16.

Subsequently, as shown in FIGS. 16 and 17, the pressure member 6 with the inserted head 3 is moved downward by a force applied onto the actuating portion 68 in the axial direction (shown by vertical arrows), such that the lowermost portion 63a of the conical outer surface 63 of the main portion 60 of the pressure member 6 enters the conical portion 51a of the passage 51 to some extent. Thereby, the outer rim with the end surface 68a of the actuating portion 68 slides along the inclined surface 57f of the tongues and spreads the tongues 57c apart, to let the actuating portion 68 pass until the end surface 68b abuts against the abutment 57e at the extension 56. In this position, the inclined surfaces 69b of the engagement portion 69 and 503b of the inner protrusion 503 of the receiving part 5 engage. Thereby, the pressure member 6 is held in this axial position and, for example, prevented or restricted from moving back upwards towards the insertion position. The lower opening 52 of the receiving part 5 is effectively narrowed by the pressure member, for example, where the pressure member blocks part of the lower opening 52, so that removal of the head 3 is not possible in this pre-locking position, but the head is still pivotable.

Figure 18:
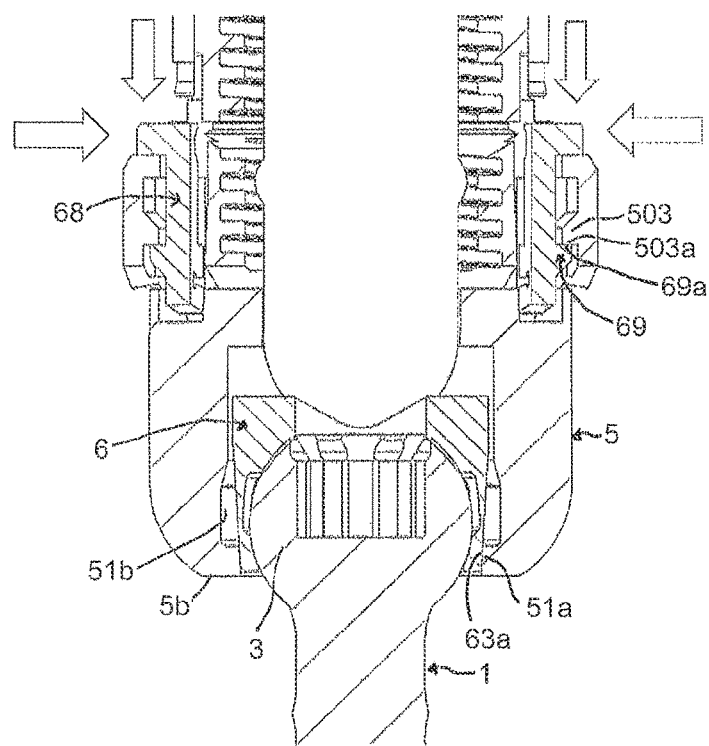
FIG. 18 shows a cross-sectional view of the polyaxial bone anchoring device of FIGS. 1 to 9, where the pressure member is in a position in which the head is provisionally locked.
Figure 19:
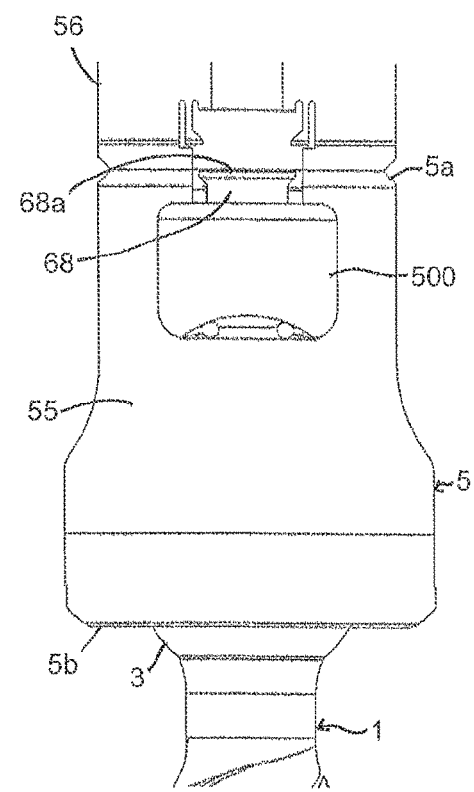
FIG. 19 is a side-view of the polyaxial bone anchoring device corresponding to FIG. 18.
Figure 20:
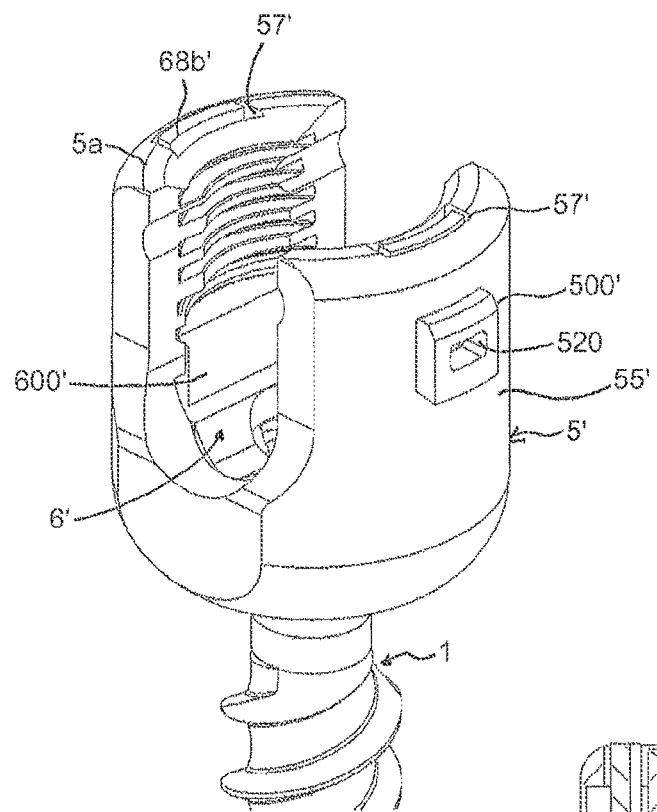
FIG. 20 shows a perspective view of a polyaxial bone anchoring device with a coupling device according to a second embodiment.
Figure 21:
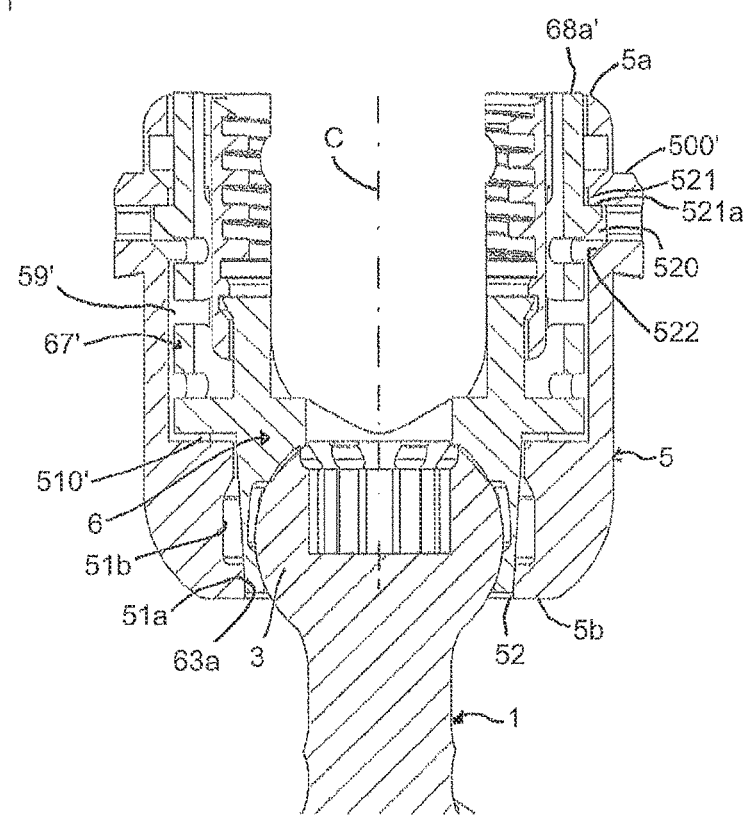
FIG. 21 shows a cross-sectional view of the polyaxial bone anchoring device of FIG. 20, the cross-section taken in a plane extending through centers of legs of a receiving part of the coupling device and including a central longitudinal axis of the receiving part.
Figure 22:
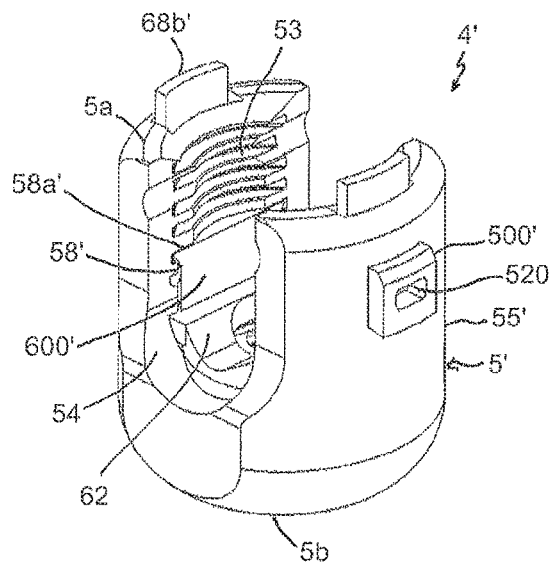
FIG. 22 shows a perspective view from a top of the coupling device of FIGS. 20 and 21, wherein a pressure member of the coupling device is in an insertion position that permits insertion of the head of the bone anchoring element.

Finally, as shown in FIGS. 18 and 19, the pressure member is moved further downward by a force applied onto the actuating portion 68 in the axial direction (shown by vertical arrows), until the engagement portions 69 of the arms snap under the inner protrusions 503 of the receiving part, so that the upper surface 69a engages the lower surface 503a of the protrusion. A slight axial resiliency of the arms 67 assists in establishing the latching connection. The conical portion 63 of the pressure member 6 has further entered the narrowing section 51a of the passage 51 of the receiving part 5, so that the head 3 is provisionally locked. The provisional locking of the head 3 can be released by exerting a transverse force onto the actuating portion as shown by the transverse arrows in FIG. 18. Due to the flexibility of the arms 67, the actuating portion is bent slightly inwards and the engagement portion 69 can move out of engagement with the inner protrusion. Thereby the latching connection can be released, for example, by moving the pressure member upwards again, and the pressure onto the head 3 can be reduced so that the head becomes pivotable again.

Finally, the pressure member 6 is pressed further into the narrowing section 51a of the passage 51, for example, by inserting the rod 100 and the fixation member 7 and tightening the fixation member 7, as shown in FIG. 2, to finally lock the head in the coupling member. Thereafter, the extensions 56 may be broken off at the weakened portions 56a.

In clinical use, usually two or more polyaxial bone anchoring devices are connected through the rod 100. In a first way of use, the bone anchoring element 1 is first inserted into bone, for example, into the pedicle of a vertebra, and the coupling device 4 is mounted on the head 3 of the bone anchoring element 1 thereafter. In a second alternative way of use, the bone anchoring element 1 and the coupling device 4 are pre-assembled and inserted together in the pre-assembled condition into the bone, for example, into pedicles of adjacent vertebrae. Prior to inserting the rod, the angular position of the coupling device relative to the bone anchoring element may be adjusted by provisionally locking and releasing the head in the coupling device as needed. For maintaining the provisional locking, neither an instrument nor the rod together with the locking member are necessary.

Referring to FIGS. 20 to 24, a second embodiment of the coupling device will be described. Parts and portions of the coupling device according to the second embodiment that are identical or similar to parts and portions of the coupling device of the first embodiment are indicated with the same reference numerals, and the descriptions thereof will not be repeated. The coupling device 4' according to the second embodiment differs from the coupling device 4 of the first embodiment in the design of the receiving part and the pressure member. The rod 100 and the locking member 7 may be the same as in the first embodiment and are not shown.

The receiving part 5' in the second embodiment does not have extensions 56. Thus, the top end 5a forms the uppermost portion of the receiving part 5'. The narrowing section 51a of the passage 51 and the accommodation space 51b, 51c are very similar to the first embodiment. Above the narrowing section 51c, a slot 59' is formed inside the legs 55'. The slot 59' extends between the outer wall of the receiving part 5' and the threaded bore 53. The slot 59' narrows towards the top end 5a such that an opening or recess 57' is formed that has a width in the circumferential direction substantially adapted to the width of an actuating portion of the pressure member 6'. In the inner wall of the channel formed by the substantially U-shaped recess 54, at an axial position below the internal thread 53, a recess 58' is formed, an upper edge of which serves as a first abutment 58a'. The first abutment 58a defines an uppermost position of the pressure member 6', as can be best seen in FIG. 23. Below the first abutment 58a', a second abutment 58b' is formed that defines a pre-locking position of the pressure member 6', in which an inserted head 3 is prevented from removal but is still pivotable.

The slot 59' is connected to the inside of the passage 51 via an opening 510' through which a portion of arms of the pressure member 6' can extend. In addition, the receiving part 5' has at the middle of each of the legs 55', at a distance from the top end 5a, a transverse hole 520 that extends from the outside into the slot 59'. A protrusion 500' is formed on the outer wall of the receiving part 5', through which the hole 520 extends. The protrusion 500' may serve as an orientation structure for facilitating engagement of the transverse hole 520 with an instrument. At an upper edge of the transverse hole 520, the inner wall of the slot 59 has a structure 521 that provides a lower surface 521*a* defining an abutment for a portion of the pressure member 6', and an inclined upper surface 521*b* along which the pressure member 6' can slide when the pressure member moves downward. At a lower edge of the transverse hole 520, another inclined surface 522 is formed that is configured to engage a correspondingly inclined surface of the pressure member 6'.

The pressure member 6' includes a main portion with a cylindrical upper section 61 with a rod receiving recess 62, and a substantially conical section 63 with the head receiving recess 64, similarly as arranged in the first embodiment. From the cylindrical portion 61, two sidewalls 600' respectively extend on the left and on the right of the rod receiving recess 62. The sidewalls 600' may be flat towards the inside and may be cylindrical towards the outside, to fit into the recesses 58' provided in the inner wall of the legs 55' of the receiving part 5'. The sidewalls 600' have a broadened rim 601' at their free end that is configured to abut against the first abutment 58*a*' of the recess 58' of the receiving part 5'. Moreover, the pressure member 6' includes two arms 67' that respectively extend from the cylindrical section 61 on the right and on the left of the rod receiving recess 62'. The arms 67' each includes a base 67*a*' that is configured to extend through the opening 510'. From the base portion 67*a*', a main portion 67*c*' protrudes vertically and may have a substantially meandering shape to provide some flexibility in the axial direction. The main portion 67*c*' may have cylindrical inner and outer surfaces. At the uppermost end of the main portion 67*c*', a circumferential projection is provided that projects outwards and forms an engagement portion 69' for engagement with the receiving part 5'. An upper surface 69*a*' of the engagement portion 69' may be substantially perpendicular to the central axis C and is configured to engage the abutment 521*a* at the upper edge of the transverse hole 520. A lower surface 69*b*' is inclined and is configured to engage the inclined surfaces 521*b* and 522 at the upper and lower edges of the transverse hole 520, respectively. From the upper surface 69*a*', an actuating portion 68' protrudes that is configured to extend into the recesses 57' of the receiving part and to project above the top end 5*a*.

Figure 23:
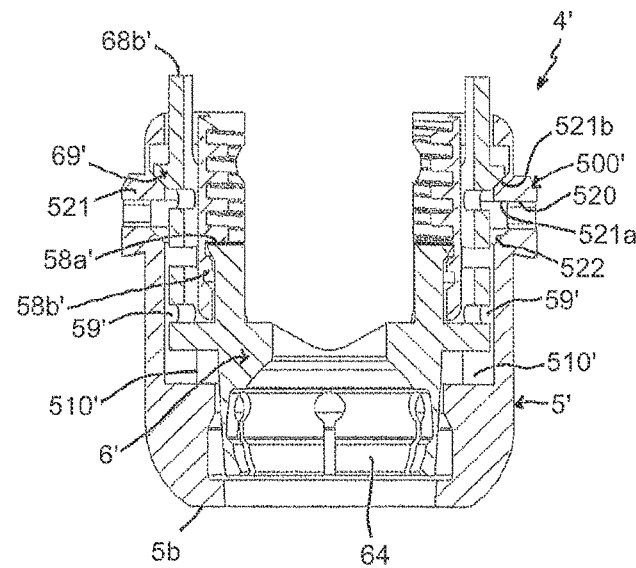
FIG. 23 shows a cross-sectional view of the coupling device of FIG. 22, the cross-section taken in a plane extending through centers of the legs and including the central longitudinal axis of the receiving part.
Figure 24:
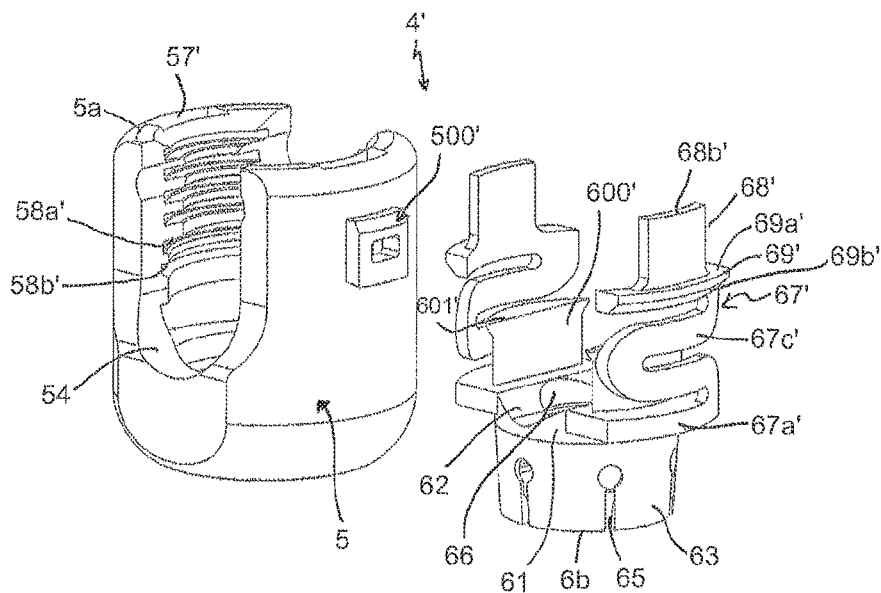
FIG. 24 shows a perspective exploded view of the coupling device of FIGS. 20 to 23, wherein the receiving part and the pressure member are separated for illustration purposes only.

In use, the pressure member 6' is configured to assume several positions with respect to the receiving part 5'. The insertion position in which the head 3 is or can be fully inserted into the head receiving recess 64 of the pressure member 6' is achieved when the upper surfaces 601' of the sidewalls 600' abut against the first abutments 58*a*' of the recesses 58', as shown in FIG. 23. The actuating portions 68' protrude above the top end 5*a*. The pre-locking position of the pressure member 6' is reached when the upper surfaces 601' of the sidewalls 600' abut against the second abutments 58*b*' of the receiving part 5'. The provisional locking position is achieved when the upper surface 69*a*' of the engagement portion 69' abuts against the lower surface 521*a* of the structure 521 at the upper edge of the transverse hole 520. The provisional locking position can be reached by pressing the actuating portion 68' downward in an axial direction. By engaging the actuating portions 68' with a tool through the holes 520 and slightly pressing the actuating portions towards the central axis, the provisional locking can be released. Final locking may be achieved by inserting the rod 100 and the locking member 7, similar to the first embodiment.

It should be noted that for both embodiments described, the insertion position and the pre-locking position may each be a first position of the pressure member in which the head is still pivotable. The provisional locking position may be a second position of the pressure member in which the head is provisionally locked.

Modifications of the above described embodiments are also conceivable. In particular, the shapes of the parts is not limited to the detailed shapes shown in the figures. Deviations may be possible and encompassed by the disclosure. It shall be noted that features of one embodiment can be also combined with features of another embodiment. For example, the coupling device may be configured to be a top loading polyaxial bone anchoring device. Hence, the opening at the bottom end of the receiving part may be smaller than a diameter of the head of the bone anchoring element, such that the bone anchoring element has to be inserted from the top end into the receiving part. In this case, the pressure member may be configured to press only from above onto an inserted head.

Instead of the locking member being a set screw, all other kinds of locking assemblies known in the art may be used. For the bone anchoring element, all types of bone anchoring elements that are suitable for anchoring in bone or a vertebra may be used, in particular, bone nails. The rod may also have various shapes and/or varying cross-sections along its length. The rod may be stiff or more flexible.

While the present invention has been described in connection with certain exemplary embodiments, it is to be understood that the invention is not limited to the disclosed embodiments, but is instead intended to cover various modifications and equivalent arrangements included within the spirit and scope of the appended claims, and equivalents thereof.

What is claimed is:

1. A coupling device for coupling a rod to a bone anchoring element, the coupling device comprising:
   a receiving part having a first end and a second end below the first end, a central axis extending through the first end and the second end, an accommodation space for accommodating a head of the bone anchoring element, an opening at the second end sized to facilitate insertion of the head therethrough, and a recess at the first end for receiving the rod, the recess forming two legs; and
   a pressure member arranged at least partially in the accommodation space, the pressure member being adjustable from a first configuration where a topmost end of the pressure member is at a first axial position and an inserted head is pivotable in the accommodation space but prevented from removal from the accommodation space through the opening, to a second configuration where the topmost end of the pressure member is at a second axial position below the first axial position and the pressure member exerts pressure onto the inserted head to provisionally lock the inserted head;
   wherein at the second configuration, a latching connection is formed between the pressure member and the receiving part to at least temporarily prevent the pressure member from being adjusted back towards the first configuration, and wherein the latching connection is releasable by exerting a force in a direction transverse to the central axis from outside the receiving part on the pressure member to adjust the pressure member from the second configuration back towards the first configuration.

2. The coupling device of claim 1, wherein the pressure member comprises a head contacting portion configured to contact the head when the pressure member is in the accommodation space, and two arms extending away from the head contacting portion, wherein each of the legs defines a slot arranged between an outer wall and an inner wall of the legs, and wherein each of the arms extends axially into a respective one of the slots.

3. The coupling device of claim 2, wherein the pressure member comprises a first engagement portion and the receiving part comprises a second engagement portion, and wherein the latching connection is established when one of the first or second engagement portions snaps below the other one of the first or second engagement portions.

4. The coupling device of claim 3, wherein the first engagement portion is located at the arms of the pressure member, and the second engagement portion is located in the slot of the receiving part.

5. The coupling device of claim 2, wherein respective free ends of the arms of the pressure member are exposed to the outside at the first end of the receiving part.

6. The coupling device of claim 2, wherein the arms are flexible, and wherein the latching connection is releasable by exerting force onto the arms in respective directions transverse to the central axis.

7. The coupling device of claim 2, wherein an outer wall of each of the legs of the receiving part comprises a transverse opening that exposes a portion of the arms of the pressure member extending into the slot to the outside for applying the forces from outside the receiving part thereto.

8. The coupling device of claim 1, wherein the pressure member is adjustable to the second configuration by exerting an axial force onto the topmost end of the pressure member.

9. The coupling device of claim 1, wherein the pressure member can further assume a third configuration that defines an insertion position where the topmost end of the pressure member is at an axial position above the first axial position and where a head is insertable through the opening into the accommodation space.

10. The coupling device of claim 1, wherein the first configuration defines a pre-locking position where the pressure member blocks a portion of the opening to prevent an inserted head from being removed from the accommodation space through the opening.

11. The coupling device of claim 1, wherein in the first configuration, the pressure member exerts a pressure on the inserted head to restrict pivoting of the head, while the recess of the receiving part remains substantially unobstructed such that a rod is insertable into and movable in the recess.

12. The coupling device of claim 11, wherein the coupling device is configured to maintain the first configuration without engaging a rod, fixation member, or instrument.

13. The coupling device of claim 1, wherein the receiving part comprises extensions that respectively extend above the legs, and wherein each of the extensions comprises an abutment for limiting upward movement of the pressure member in the first configuration.

14. The coupling device of claim 1, wherein the receiving part and the pressure member are inseparably interconnected with each other.

15. The coupling device of claim 1, wherein the receiving part and the pressure member are monolithically formed with one another.

16. The coupling device of claim 1, wherein the receiving part and the pressure member are formed together by using an additive manufacturing method.

17. A bone anchoring device comprising:
the coupling device of claim 1; and
the bone anchoring element comprising the head and a shank for anchoring in bone, wherein the head has a spherically-shaped outer surface portion that at least partially faces a free end of the shank to facilitate pivoting in the accommodation space.

18. A coupling device for coupling a rod to a bone anchoring element, the coupling device comprising:
a receiving part having a first end and a second end below the first end, a central axis extending through the first end and the second end, an accommodation space for accommodating a head of the bone anchoring element, an opening at the second end, a recess at the first end for receiving the rod, the recess forming two legs, a downwardly facing surface, and an upwardly facing surface monolithically formed with the downwardly facing surface; and
a pressure member arranged at least partially in the accommodation space, the pressure member being movable axially relative to the receiving part from a first axial position where an inserted head is pivotable in the accommodation space to a second axial position below the first axial position where the pressure member exerts pressure onto the inserted head to provisionally lock the inserted head;
wherein a range of the axial movement of the pressure member is limited in the receiving part by the downwardly and upwardly facing surfaces, and wherein the receiving part and the pressure member are only separable from one another by permanently deforming or damaging at least one of the receiving part or the pressure member.

19. A coupling device for coupling a rod to a bone anchoring element, the coupling device comprising:
a receiving part having an accommodation space for accommodating a head of the bone anchoring element, an opening at the second end, and a recess at the first end for receiving the rod, the recess forming two legs; and
a pressure member arranged at least partially in the accommodation space, the pressure member being movable relative to the receiving part from a first axial position where an inserted head is pivotable in the accommodation space to a second axial position below the first axial position where the pressure member exerts pressure onto the inserted head to provisionally lock the inserted head;
wherein the pressure member is formed at a position relative to the receiving part where a first abutting surface of the receiving part prevents axial movement of the pressure member in a first direction and a second abutting surface of the receiving part prevents axial movement of the pressure member in a second direction opposite the first direction, and wherein the receiving part and the pressure member are only separable from one another by permanently deforming or damaging at least one of the receiving part or the pressure member.

20. The coupling device of claim 19, wherein the receiving part and the pressure member are formed together using an additive manufacturing method.

21. The coupling device of claim 19, wherein the receiving part and the pressure member are formed as a monolithic unit, and wherein a portion of the monolithic unit is thereafter removed to render the receiving part and the pressure member movable relative to one another but only separable from one another by permanently deforming or damaging at least one of the receiving part or the pressure member.

* * * * *